United States Patent [19]

Hall et al.

[11] Patent Number: 5,723,495
[45] Date of Patent: Mar. 3, 1998

[54] BENZAMIDOXIME PRODRUGS AS ANTIPNEUMOCYSTIC AGENTS

[75] Inventors: James E. Hall, Chapel Hill; Richard R. Tidwell, Pittsboro, both of N.C.; David W. Boykin, Atlanta, Ga.

[73] Assignees: The University of North Carolina at Chapel Hill, Chapel Hill, N.C.; Georgia State University, Atlanta, Ga.

[21] Appl. No.: 558,716

[22] Filed: Nov. 16, 1995

[51] Int. Cl.$^6$ .................................................. A61K 31/165
[52] U.S. Cl. .................. 514/633; 514/398; 514/438; 514/471; 548/304.7; 548/305.8; 564/229
[58] Field of Search ............................ 514/633; 564/229

[56] References Cited

U.S. PATENT DOCUMENTS

| | | | |
|---|---|---|---|
| 2,425,223 | 8/1947 | Barber | 260/501 |
| 2,449,724 | 9/1948 | Short et al. | 260/564 |
| 2,851,495 | 9/1958 | Jensch et al. | 260/564 |
| 3,767,616 | 10/1973 | Zellner | 260/47 |
| 4,034,010 | 7/1977 | Hamano et al. | 260/564 |
| 4,064,169 | 12/1977 | Hamano et al. | 260/564 |
| 4,237,168 | 12/1980 | Reifschneider | 424/326 |
| 4,546,113 | 10/1985 | Glazer | 514/636 |
| 4,933,347 | 6/1990 | Tidwell et al. | 514/256 |
| 5,262,157 | 11/1993 | Bernard et al. | 424/45 |
| 5,364,615 | 11/1994 | Debs et al. | 424/45 |
| 5,366,726 | 11/1994 | Debs et al. | 424/45 |

FOREIGN PATENT DOCUMENTS

| | | |
|---|---|---|
| 2081401 | 12/1971 | France . |
| WO 95/08540 | 3/1995 | WIPO . |

OTHER PUBLICATIONS

Arch. Pharm (Weinheim) 325, 61–62, 1992.

B. Clement et al.; *Amidoximes of Pentamidine: Synthesis, Trypanocidal and Leishmanicidal Activity*, Arzneim.-Forsch/Drug Res. 35(II): 1009–1014 (1985).

B. Clement et al.; *Reduction of Amidoxime Derivatives to Pentamidine in vivo*, Arch. Pharm. (Weinheim) 325: 61–62 (1992).

B. Clement et al.; *N-Hydroxylation of the Antiprotozoal Drug Pentamidine Catalyzed by Rabbit Liver Cytochrome P–450 2C3 or Human Liver Microsomes, Microsomal Retroreduction, and Further Oxidative Transformation of the Formed Amidoximes*, Drug Metabolism and Diposition 22:486–497 (1994).

A.T. Fuller et al.; *Chemotherapeutic Agents if the Sulphone Type. Part II. Sulphones Related to Benzamidine and Benzylamine*, J. Chem. Soc. 633–640 (1945).

C.H. Andrewes et al.; *Experimental chemotherapy of typhus. Anti–rickettsial action of p–sulphonamidobenzamidine and related compounds*, Proc. Royal Soc. (London) 133B:20–62 (1946).

N.P. Buu–Hoi et al.; *Une nouvelle famille de composes tuberculostatiques: les amidoximes*, Experientia 10:169 (1954).

P. Chabrier et al.; *Nouvelles recherches sur les rapports entre structure chimique, activite' antibacterienne, antifungique et toxicite', dans la serie des esters de l'acide dithiocarbamique N–disubstitue'*, Ann. Pharm. Franc. 14:720–728 (1956).

I.D. Lamb et al.; *Some Amidines and Amidoximes with Trypanocidal Activity*, J. Chem. Soc. 1253–1257 (1939).

Primary Examiner—Yogendra N. Gupta
Attorney, Agent, or Firm—Myers Bigel Sibley & Sajovec, LLP

[57] ABSTRACT

A method of treating *Pneumocystis carinii* pneumonia in a subject in need of such treatment is disclosed. The method comprises orally administering to the subject a bis-benzamidoxime of formula I:

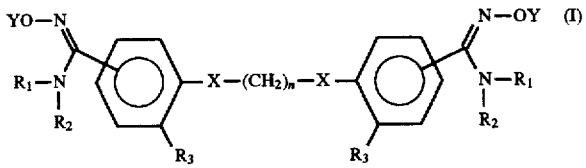

wherein $R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl; $R_3$ is H, loweralkyl, oxyalkyl, alkoxyalkyl, hydroxyalkyl, cycloalkyl, aryl, aminoalkyl, alkylaminoalkyl or halogen; n is from 2 to 6; X is O, N, or S; and Y is H or loweralkyl, or a pharmaceutically acceptable salt thereof, that is reduced in the subject to produce a benzamidine having anti-*P. carinii* activity. The method of the present invention may alternatively comprise intravenously administering to the subject an active compound as disclosed herein. Pharmaceutical formulations and active compounds useful in the practice of the present invention are also disclosed.

3 Claims, No Drawings

BENZAMIDOXIME PRODRUGS AS ANTIPNEUMOCYSTIC AGENTS

The present invention was made with Government support under Grant Number 5-UO1-AI33363-03 from the National Institutes of Health. The Government has certain rights to this invention.

FIELD OF THE INVENTION

The present invention relates to methods useful in combating *Pneumocystis carinii* pneumonia and prodrug compounds useful therefor.

BACKGROUND OF THE INVENTION

Pentamidine is used for the treatment of *Pneumocystis carinii* pneumonia, or "PCP". The importance of pentamidine has dramatically escalated recently due to the marked increase of patients suffering from PCP. The increase in the afflicted patient population is an unfortunate consequence of the increasing presence of the Acquired Immunodeficiency Syndrome ("AIDS"). It is now estimated that approximately 70 percent of AIDS patients contract PCP. Because of the high incidence of PCP in AIDS patients, pentamidine has found utility not only in the treatment of PCP, but also as prophylaxis, in preventing or delaying the initial onset or recurrence of PCP, especially in AIDS patients. Currently, pentamidine is most commonly administered as a therapeutic agent by intravenous infusion and as a prophylactic agent by aerosol dosage.

However, an unfortunate side effect of pentamidine is its toxicity. Some fatalities have been attributed to severe hypotension, dysglycemia, and cardiac arrhythmias in patients treated with pentamidine. Contrawise, insufficient dosage may result in dissemination of disease beyond the lung, an occurrence which is associated with a poor prognosis. Therapeutic drug monitoring is not used because of the cost and complexity of the currently available assay techniques which require the extraction of plasma and High Performance Liquid Chromatography (HPLC) analysis. As a result, the toxicity of pentamidine is a significant concern, which is driving the market toward the development of pentamidine substitutes capable of avoiding or minimizing the undesirable side effects associated with the use of pentamidine. See, e.g., J. Spychala et al., *Eur. J. Med. Chem.* 29, 363–367 (1994); I. O. Donkor et al., *J. Med. Chem.* 37, 4554–4557 (1994); R. R. Tidwell et al., *J. Protozool.* 6, 148S–150S (1991).

Accordingly, it is an object of the present invention to provide new compounds useful in the treatment of *P. carinii* pneumonia.

SUMMARY OF THE INVENTION

A method of treating *Pneumocystis carinii* pneumonia in a subject in need of such treatment is disclosed. The method comprises orally administering to the subject a bis-benzamidoxime, or a pharmaceutically acceptable salt thereof (hereinafter referred to as the "active compound"), that is reduced in the subject to produce a benzamidine having anti-*P. carinii* activity. The method of the present invention may alternatively comprise intravenously administering to the subject an active compound as disclosed herein.

A second aspect of the present invention is a pharmaceutical formulation comprising, in combination with a pharmaceutically acceptable carrier, a bis-benzamidoxime, or a pharmaceutically acceptable salt thereof, that is reduced in a mammalian subject after administration thereto to produce a benzamidine having anti-*Pneumocystis carinii* activity, subject to the proviso that said bis-benzamidoxime is not 1,5-bis(4'-(N-hydroxyamidino) phenoxy)pentane.

A third aspect of the present invention are active compounds useful in carrying out a therapeutic method of the present invention.

A fourth aspect of the present invention is the use of an active compound as disclosed herein for the manufacture of a medicament useful in carrying out a therapeutic method of treatment as given above.

DETAILED DESCRIPTION OF THE INVENTION

Active compounds of the present invention are, in general, the bis-benzamidoxime derivatives of benzamidines that have anti-*Pneumocystis carinii* activity. The benzamidines having anti-*P. carinii* activity may be mono-benzamidines, wherein one amidoxime group of the bis-benzamidoxime derivative is reduced; alternatively, they may be bis-benzamidines wherein both amidoxime groups of the bis-benzamidoxime derivative are reduced. Thus, bis-benzamidoxime derivatives of benzamidines having anti-*P. carinii* activity are an aspect of the present invention. Examples of such benzamidines are disclosed in, e.g., U.S. Pat. Nos. 2,277,861 to Ewins et al.; 2,410,796 to Newberry et al.; 4,933,347 to Tidwell et al.; and PCT application No. US93/09477 (applicant specifically intends the disclosure of these and all other patent references cited herein to be incorporated herein by reference).

As used herein, the term "cycloalkyl" as used herein refers to C3 to C6 cyclic alkyl, such as cyclopropyl, cyclobutyl, cyclopentyl, and cyclohexyl. Cyclohexyl and cyclopentyl are currently preferred. The term "aryl" as used herein refers to C3 to C10 cyclic aromatic groups such as phenyl, naphthyl, and the like, and includes substituted aryl groups such as tolyl. The term "hydroxyalkyl" as used herein refers to C1 to C4 linear or branched hydroxy-substituted alkyl, i.e., —CH$_2$OH, —(CH$_2$)$_2$OH, etc. The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc. The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

One preferred group of compounds useful in the practice of the present invention are bis-benzamidoximes of the formula I:

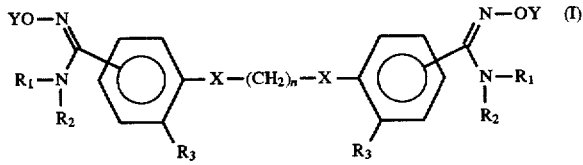

wherein:

R$_1$ and R$_2$ are each independently selected from the group consisting of H, loweralkyl, oxyalkyl, alkoxyalkyl, cycloalkyl, aryl, hydroxyalkyl, aminoalkyl or alkylaminoalkyl;

R$_3$ is H, loweralkyl, oxyalkyl, alkoxyalkyl hydroxyalkyl, cycloalkyl, aryl, aminoalkyl, alkylaminoalkyl or halogen;

n is from 2 to 6;

X is O, N, or S; and

Y is H or loweralkyl;

or pharmaceutically acceptable salts thereof.

A second group of compounds useful in the practice of the present invention are bis-benzamidoximes of the formula II:

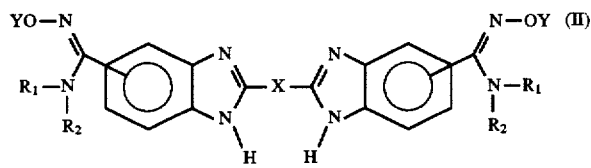

wherein:

$R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl;and X is C1 to C12 linear or branched, saturated or unsaturated alkyl containing up to four double bonds; and Y is H or loweralkyl;

or pharmaceutically acceptable salts thereof.

A third preferred group of compounds useful in the practice of the present invention are bis-benzamidoximes of the formula III:

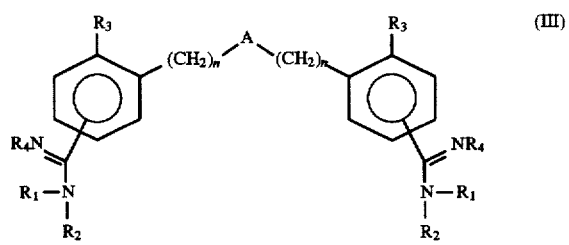

wherein:

$R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl; $R_3$ is H, loweralkyl, oxyalkyl, alkoxyalkyl, hydroxyalkyl, cycloalkyl, aryl, aminoalkyl, alkylaminoalkyl or halogen;

$R_4$ is —OH, or $R_1$ and $R_4$ together represent

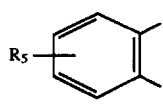

wherein $R_5$ is

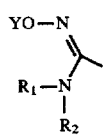

Y is H or loweralkyl;

n is an integer from 0 to 2; and

A is a heterocyclic aromatic group selected from the group consisting of:

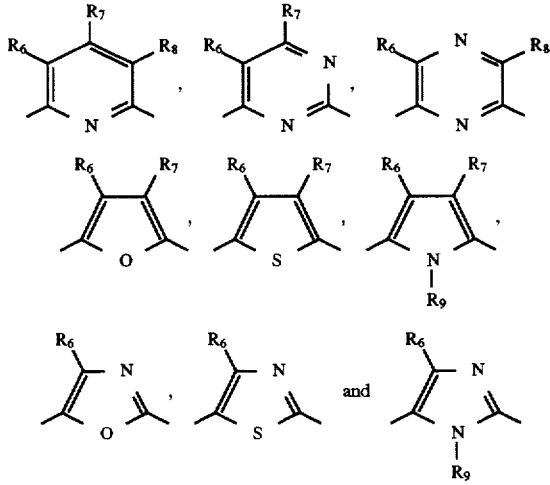

wherein $R_6$, $R_7$ and $R_8$ are each independently selected from the group consisting of H, loweralkyl, halogen, oxyalkyl, oxyaryl, or oxyarylalkyl;

$R_9$ is hydrogen, loweralkyl, hydroxy, aminoalkyl or alkylaminoalkyl;

or pharmaceutically acceptable salts thereof.

A fourth preferred group of compounds useful in the practice of the present invention are bis-benzamidoximes of the formula IV:

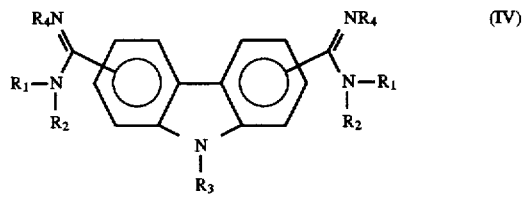

wherein:

$R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl;

$R_3$ is H, loweralkyl, oxyalkyl, alkoxyalkyl, hydroxyalkyl, cycloalkyl, aryl, aminoalkyl, alkylaminoalkyl or halogen;

$R_4$ is —OH, or $R_1$ and $R_4$ together represent

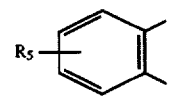

wherein $R_5$ is

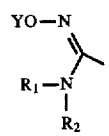

Y is H or loweralkyl;

n is an integer from 0 to 2;

or pharmaceutically acceptable salts thereof.

As noted above, the methods of the present invention are useful for treating *P. carinii* pneumonia. The methods of the present invention are useful for treating these conditions in that they inhibit the onset, growth, or spread of the condition, cause regression of the condition, cure the condition, or otherwise improve the general well-being of a subject inflicted with, or at risk of contracting the condition.

Subjects to be treated by the methods of the present invention are typically human subjects, although the methods of the present invention may be useful with any suitable subject known to those skilled in the art.

As noted above, the present invention provides pharmaceutical formulations comprising the aforementioned active compounds, or pharmaceutically acceptable salts thereof, in pharmaceutically acceptable carriers for oral, intravenous, or aerosol administration as discussed in greater detail below.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 100 mg/kg will have therapeutic efficacy, with all weights being calculated based upon the weight of the active base, including the cases where a salt is employed. A dosage from about 10 mg/kg to about 50 mg/kg may be employed for oral administration. The duration of the treatment is usually once per day for a period of two to three weeks or until the P. carinii pneumonia is essentially controlled. Lower doses given less frequently can be used to prevent or reduce the incidence of recurrence of the infection.

In accordance with the present method, an active compound as described herein, or a pharmaceutically acceptable salt thereof, may be administered orally as a solid or as a liquid, or may be administered intravenously. Alternatively, the active compound or salt may also be administered by inhalation. When administered through inhalation the active compound or salt should be in the form of a plurality of solid particles or droplets having a particle size from about 0.5 to about 5 microns, preferably from about 1 to about 2 microns.

Besides providing a method for treating P. carinii pneumonia, the active compounds of the present invention also provide a method for prophylaxis against P. carinii pneumonia in an immunocompromised patient, such as one suffering from AIDS, who has had at least one episode of P. carinii pneumonia, but who at the time of treatment is not exhibiting signs of pneumonia. As P. carinii pneumonia is an especially potentially devastating disease for immunocompromised patients it is preferable to avoid the onset of P. carinii pneumonia, as compared to treating the disease after it has become symptomatic. Accordingly, the present invention provides a method for the prophylaxis against P. carinii pneumonia comprising administering to the patient a prophylactically effective amount of the active compound or a pharmaceutically acceptable salt thereof. The forms for administration of the compound or salt in accordance with this method may be the same as utilized for the purpose of actually treating a patient suffering from P. carinii pneumonia.

An additional useful aspect of the present invention is a method for prophylaxis against even an initial episode of P. carinii pneumonia in an immunocompromised patient who has never experienced an episode of P. carinii pneumonia. In this respect, a patient who has been diagnosed as being immunocompromised, such as one suffering from AIDS or ARC (AIDS related complex), even before the onset of an initial episode of P. carinii pneumonia, may avoid or delay suffering from the infection by having administered a prophylactically effective amount of an active compound of the present invention or a pharmaceutically acceptable salt thereof. The compound or salt may be administered in the same fashion as in the treatment of patients suffering from P. carinii pneumonia.

In the manufacture of a medicament according to the invention (a "formulation"), active agents or the pharmaceutically acceptable salts thereof (the "active compound") are typically admixed with, inter alia, an acceptable carrier. The carrier must, of course, be acceptable in the sense of being compatible with any other ingredients in the formulation and must not be deleterious to the subject. The carrier may be solid or liquid, or both, and is preferably formulated with the compound as a unit-dose formulation, for example, a tablet, which may contain from 0.05% to 99% by weight of the active compound. One or more active compounds may be incorporated in the formulations of the invention (e.g. the formulation may contain one or more additional anti-P. carinii agents as noted above), which formulations may be prepared by any of the well-known techniques if pharmacy consisting essentially of admixing the components, including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

In addition to the active compounds or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Other pharmaceutical compositions may be prepared from the water-insoluble active compounds, or salts thereof, such as aqueous base emulsions. In such an instance, the composition will contain a sufficient amount of pharmaceutically acceptable emulsifying agent to emulsify the desired amount of the active compound or salt thereof. Particularly useful emulsifying agents include phosphatidyl cholines, and lecithin.

Further, the present invention provides liposomal formulations of the active compounds and salts thereof. The technology for forming liposomal suspensions is well known in the art. When the active compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the active compounds or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired active compound or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid active compound, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble active compound of the present invention or a salt thereof, in a carrier which comprises water. A surfactant may be present which lowers the surface tension of the formulation sufficiently to result in the formation of droplets within the desired size range when subjected to nebulization.

Formulations of the present invention suitable for intravenous administration comprise sterile aqueous and non-aqueous injection preparations of the active compound, which preparations are preferably isotonic with the blood of the intended recipient. These preparations may include anti-oxidants, buffers, bacteriostats, and solutes that render the formulation isotonic with the blood of the intended recipient. Aqueous and non-aqueous sterile suspensions may include suspending agents and thickening agents. The formulations may be presented in unit/dose or multi-dose containers, for example sealed ampules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

Examples of active compounds of the present invention include, but are not limited to:

(1) 1,5-bis(4'-(N-hydroxyamidino)phenoxy)pentane
(2) 1,3-bis(4'-(N-hydroxyamidino)phenoxy)propane
(3) 1,3-bis(2'-methoxy-4'-(N-hydroxyamidino)phenoxy) propane
(4) 1,4-bis(4'-(N-hydroxyamidino)phenoxy)butane
(5) 1,5-bis(4'-(N-hydroxyamidino)phenoxy)pentane di-hemimaleinate
(6) 1,3-bis(4'-(4-hydroxyamidino)phenoxy)propane di-hemimaleinate
(7) 1,3-bis(2'-methoxy-4'-(N-hydroxyamidino)phenoxy) propane di-hemimaleinate
(8) 1-(4'-(N-hydroxyamidino)phenoxy)butane bis-maleinate Compounds employed in carrying out the present invention may be prepared in accordance with techniques known to those skilled in the art, particularly in light of the disclosure and examples set forth below.

As indicated, the compounds used in the present invention may be present as pharmaceutically acceptable salts. Such salts include the maleinate, gluconate, lactate, acetate, tartarate, citrate, phosphate, borate, nitrate, sulfate, and hydrochloride salts.

The salts of the present invention may be prepared, in general, by reacting two equivalents of the pyrimidine base compound with the desired acid, in solution. After the reaction is complete, the salts are crystallized from solution by the addition of an appropriate amount of solvent in which the salt is insoluble.

As noted above, the active compounds of the present invention may be prepared according to methods known in the art. For example, the active compounds above may be prepared by first synthesizing known bis-nitriles using Allen's procedure for alkylation of phenols. See J. N. Ashley et al., *J. Chem. Soc.* 103–116 (1942); C. F. H. Allen et al. *Org. Synth. Coll.* III, 141–41 (1955). The active compounds can then be obtained by using variations of the known technique of Clement and Raether and by using appropriate reagents. See B. Clement and W. Raether, *Arzneim. Forsch.* 35, 1009–1014 (1985). Scheme 1, below, outlines the foregoing procedures for preparing active compounds of the present invention.

Subjects with other microbial infections, in addition to *P. carinii* pneumonia, may also be treated by the methods of the present invention in the same manner as described above. These infections may be caused by a variety of microbes, including fungi, algae, protozoa, bacteria, and viruses. Exemplary microbial infections that may be treated by the method of the present invention include, but are not limited to, infections caused by *Giardia lamblia, Cryptosporidium parrum, Cryptococcus neoformans, Candida albicans, Candida tropicalis, Salmonella typhimurium, Plasmodium falciparum,* and *Leishmania mexicana amazonensis.*

The following examples are provided to illustrate the present invention, and should not be construed as limiting thereon. In these examples, mM means millimolar, mL means milliliters, mm means millimeters, cm means centimeters, °C. means degrees Celsius, g means grams, kg means kilograms, m.p. means melting point, MHz means megahertz, M means molar, h means hours, NMR means nuclear magnetic resonance, FAB means fast atom bombardment, DMF means dimethylformamide, EtOH means ethyl alcohol, DMSO means dimethylsulfoxide, HPLC means high-pressure liquid chromatography, TLC means thin-layer chromatography, dec means decomposition point.

In the following examples, uncorrected melting points were measured on a Thomas Hoover capillary melting point apparatus or a Mel-Temp II apparatus. $^1$H NMR and $^{13}$C NMR spectra were recorded on Jeol GX-270, Bruker 300, Varian Gemini 300 and XL 400 spectrometers. Chemical shifts are expressed in parts per million relative to tetramethylsilane or sodium 3-(trimethylsilyl)propionate. Anhydrous ethanol was distilled over Mg immediately prior to use. Reaction products were dried over $P_2O_5$ at 77° or 110° C. at 0.2 mm Hg. Unless stated otherwise, reactions were monitored by TLC on silica or by reverse phase HPLC. HPLC chromatograms were recorded on a Hewlett-Packard 1090 chromatograph using a Dupont Zorbax Rx C8 column (4.6 mm×25 cm) and UV detection (230 nm). Mobile phases consisted of mixtures of acetonitrile (5–67.5% v/v) in water containing 10 mM tetramethylammonium chloride, 10 mM sodium heptanesulfonate, and 2.2 mM phosphoric acid. Chromatographic data were recorded and analyzed with a Hewlett-Packard 3396 integrator. Electron impact mass spectra were recorded on a VG 70-SE, a VG 70-SEQ Hybrid, or a JMS 0-100 double-focusing spectrometer. FAB mass spectra were recorded on a VG 70-SEQ Hybrid spectrometer (cesium ion gun, 30 KV). Microanalyses were performed by Atlantic Microlab, Norcross, Ga.

In Examples 1–6, the following compound designations are used throughout.

EXAMPLE 1

Synthesis of bis-benzonitriles 2

42 mmol of 1,5-dibromopentane (for preparing pentamidine derivatives) or 1,3-dibromopentane (for preparing propamidine derivatives) is added to a suspension of 84 mmol of the appropriate 4-hydroxybenzonitrile (1) and 126 mmol of $K_2CO_3$ in 200 mL DMF. The mixture is warmed to 65°–70° C. and allowed to stir overnight. The mixture is diluted in 400 mL of $H_2O$, the precipitated product is collected and washed with $H_2O$. The crude bis-benzonitriles (2) are recrystallized from ethanol.

EXAMPLE 2

Synthesis of bis-benzamidoximes 32 mL of a 21% sodium ethoxide (in ethanol) solution is added to a hot solution of 98 mmol of $NH_2OH.HCl$ in 100 mL ethanol. The NaCl is removed by filtration and the filtrate is entered directly into a flask containing 10 mmol of the appropriate bis-benzonitrile (2). The mixture is warmed to reflux and allowed to stir for 5 hrs, cooled to room temperature and permitted to stand overnight. The precipitated product is collected, washed with ethanol and dried in a vacuum desiccator. The following spectral and analytic data were collected:

Compound (3a): m.p.>164°–65° C.; (literature value: 163° C.; see R. R. Tidwell et al., J. Med Chem. 26, 294–98 (1983)); 3.6 g, 60%.

Novel Compound (3b): m.p. 162° C., (1.6 g, 47%); $^1$H-NMR (300 MHz, DMSO) δ 2.18 (m, 2H), 4.16 (t, J=5.9 Hz, 4 H), 5.72 (s, 4H), 6.95 (d, 4H, J=8.6 Hz), 7.59 (d, 4H, J=8.6 Hz), 9.45 (s, 2H) ppm; FABMS m/z 345 (M+H); Exact mass calculated for $C_{17}H_{21}N_{14}O_4$: 345.1563; found: 345.1557; Anal. ($C_{17}H_{21}N_{14}O_4$): C, H, N.

Novel Compound (3c): m.p. 117° C. (2.9 g, 73%); $^1$H-NMR (300 MHz, DMSO) δ 2.17 (m, 2H), 4.14 (t, 4H, J=5.9 Hz), 5.74 (s, 4H), 6.98 (d, 2H, J=8.4 Hz), 9.46 (s, 2H) ppm; FABMS m/z 405 (M+H); Exact mass calculated for $C_{19}H_{25}N_4O_6$: 405.1774; found: 405.1795; Anal. ($C_{19}H_{25}N_4O_6.(H_2O)_{1.3}$: C, H, N.

Novel Compound (3d): m.p. 200° C. (dec) (1.0 g, 33%); $^1$H-NMR (300 MHz, DMSO) δ 1.87 (s, 2H), 4.05 (s, 2H), 5.72 (s, 4H), 6.95 (d, 4H, J=8.7 Hz), 7.60 (d, 2H, J=8.7 Hz), 9.45 (s, 2H) ppm; FABMS m/z 359 (M+H); Anal. ($C_{18}H_{22}N_4O_4$): C, H, N.

| Compound # | Name |
|---|---|
| 1 | 4-hydroxybenzonitrile |
| 2 | bis-benzonitrile |
| 3a | 1,5-bis(4'-(N-hydroxyamidino)phenoxy)pentane |
| 3b | 1,3-bis(4'-(N-hydroxyamidino)phenoxy)propane |
| 3c | 1,3-bis(2'-methoxy-4'-(N-hydroxyamidino)phenoxy)propane |
| 3d | 1,4-bis(4'-(N-hydroxyamidino)phenoxy)butane |
| 4a | 1,5-bis(4'-(N-hydroxyamidino)phenoxy)pentane di-hemimaleinate |
| 4b | 1,3-bis(4'-(4-hydroxyamidino)phenoxy)propane di-hemimaleinate |
| 4c | 1,3-bis(2'-methoxy-4'-(N-hydroxyamidino)phenoxy)propane di-hemimaleinate |
| 4d | 1-(4'-(N-hydroxyamidino)phenoxy)butane bis-maleinate |

Further elemental analysis data is shown in Table 1.

TABLE 1

Elemental Analyses of Novel Amidoximes

| Compound | Molecular Formula | Calculated | Found |
|---|---|---|---|
| 3b | $C_{17}H_{20}N_4O_4$ | C:59.30; H:5.81; N:16.28 | C:59.12; H:5.86; N:16.00 |
| 3c | $C_{19}H_{24}N_4O_6.(H_2O)_{1.3}$ | C:53.34; H:6.27; N:13.10 | C:53.64; H:6.01; N:12.71 |
| 3d | $C_{18}H_{22}N_4O_4$ | C:59.13; | C:59.75; H:6.24; |

TABLE 1-continued

Elemental Analyses of Novel Amidoximes

| Compound | Molecular Formula | Calculated | Found |
|---|---|---|---|
| 4b | $C_{25}H_{28}N_4O_{12} \cdot (H_2O)_{1.6}$ | H:6.29; N:15.32 C:49.59; H:5.20; N:9.26 | N:14.67 C:49.39; H:4.99; N:9.59 |
| 4c | $C_{27}H_{32}N_4O_{14} \cdot (H_2O)$ | C:49.53; H:5.26; N:10.30 | C:53.88; H:5.31; N:10.03 |
| 4d | $C_{18}H_{22}N_4O_4 \cdot 1.60 C_4H_4O_4$ | C:58.21; H:6.65; N:12.93 | C:57.99; H:6.55; N:13.29 |

EXAMPLE 3

Synthesis of bis-maleinates 2.7 mmol of bis-amidoxime 3 was taken up in 20 mL hot THF. Insoluble impurities (monoadducts) are removed by addition of 20 mL of a THF solution of either 6.8 mmol or 3.6 mmol of maleic acid. The resulting precipitate is collected and washed with ether/ethanol and then ether to give the bis-hemimaleinates as colorless powders in most cases. The following analytical and spectral data are observed:

Compound (4a): m.p. 118°–120° C. (literature 115°–120° C., see R. R. Tidwell et al., *J. Med Chem.* 26, 294–98 (1983)). (1.2 g, 75%).

Novel Compound (4b): m.p. 135° C. (dec) (800 mg, 91%); Anal. $(C_{25}H_{28}N_4O_{12} \cdot (H_2O)_{1.6})$ C,H,N.

Novel Compound (4c): m.p. 134° C. (dec) (700 mg, 86%) Anal. $[C_{27}H_{32}N_4O_{14} \cdot (H_2O)]$ C, H, N.

Novel Compound (4d): m.p. 154° C. (1.1 g, 67%) Anal. $[C_{18}H_{22}N_4O_4$ (C,H,N).

Further elemental analysis data is shown in Table 1.

EXAMPLE 6

Activity of Novel Compounds Against *Pneumocystis carinii*

The activity of the compounds against *P. carinii* was carried out according to an established method. See Tidwell, R. R., et al., *J. Protozool.* 36, 74S–76S (1989); Jones, S. K., et al., *Antimicrob. Agents Chemother.* 34, 1026–1030 (1990); Tidwell, R. R., et al., Antimicrob. Agents Chemother. 37, 1713–1716 (1993). Briefly, male Sprague-Dawley rats (barrier raised, not certified virus-free) weighing 150–200 g each, were obtained (Hilltop Laboratories, Scottsdale, Pa.). Immediately upon arrival, the animals were caged individually and begun on a low protein (8%) diet and on drinking water containing tetracycline (0.5 mg/mL) and dexamethasone (1.0 µ/mL). This regimen was continued for eight weeks. At the beginning of the seventh week, animals were divided into groups of 8 or more, and the test compounds were administered for 14 days. Saline and pentamidine-treated groups were included as controls.

Animals were sacrificed at the end of the eighth week by chloroform inhalation. The left lung was weighed, ground through a No. 60 wire mesh screen, and suspended 1:10 (wt/vol) in 10 mM β-mercaptoethanol-Hanks' balanced salts solution (HBSS) without cations. Slides were prepared by spotting 5 µL of lung homogenate diluted 1:10 in HBSS with β-mercaptoethanol and allowed to air dry. The slides were stained with cresyl violet, and the cysts were counted by a blinded protocol. The number of cysts per gram of original lung tissue was calculated, and the groups were reported as the percentages of saline-treated controls.

The anti-*P. carinii* value for each compound is expressed as the percent of cysts in the treatment group as compared to the saline control group. Values are also compared to a positive control group consisting of animals treated intravenously with pentamidine.

All four aromatic amidoximes tested were active against *P. carinii* when administered orally by garage once daily for 14 days (see Table 2). Mean cyst counts for each test group were significantly reduced compared to the saline control group. Compounds 4b, 4c and 4d were most active. The corresponding aromatic amidines, in contrast, had reduced or no anti-*P.carinii* activity when given orally (see Table 3). The only diamidine with significant oral activity was compound 10. Its corresponding amidoxime (compound 4c) was more active (see Table 2).

All aromatic amidoximes tested had excellent anti-*P. carinii* activity when given intravenously. Mean cyst counts for Compounds 4a–4d were significantly reduced compared to saline controls (see Table 2), and were also lower than cyst counts for the intravenous pentamidine group. The diamidine compounds 9 through 11 were previously shown to have intravenous activity (see Table 3). Direct comparisons of diamidine and corresponding diamidoxime (Compounds 4b, 4c, 4d) intravenous activities cannot be made, however, as the intravenous activities of diamidines were previously evaluated by a different score method and at slightly different doses. However, the data indicates that the amidoximes compare favorably with regard to intravenous efficacy.

TABLE 2

Activity of aromatic amidoximes against *Pneumocystis carinii* pneumonia.

$$\text{HON=C(NH}_2\text{)-C}_6\text{H}_3\text{(R)-O-(CH}_2\text{)}_n\text{-O-C}_6\text{H}_3\text{(R)-C(NH}_2\text{)=NOH}$$

| Compound | n | R | ORAL DOSING[a] cysts/g lung ± S.E. (×10$^6$) | % saline | # rats | IV DOSING[b] cysts/g lung ± S.E. (×10$^6$) | % saline | # rats |
|---|---|---|---|---|---|---|---|---|
| Saline | — | — | 37.78 + 9.49 | 100.00 | 6 | 32.36 + 11.03 | 100.00 | 6 |
| Pentamidine | — | — | 64.36 + 25.35 | 170.35 | 6 | 0.28 + 0.08[c] | 0.87 | 6 |
| 4 a | 5 | H | 7.28 + 5.22[c] | 19.27 | 5 | 0.05 + 0.01[c] | 0.15 | 6 |
| 4 b | 3 | H | 0.85 + 0.36[c] | 2.25 | 5 | 0.01 + 0.003[c] | 0.03 | 6 |
| 4 c | 3 | OCH$_3$ | 1.40 + 1.18[c] | 3.71 | 6 | 0.01 + 0.002[c] | 0.03 | 3 |
| 4 d | 4 | H | 0.54 + 0.23[c] | 1.43 | 5 | 0.04 + 0.02[c] | 0.12 | 6 |

[a] Oral doses administered daily for 14 days by gavage @33 μmol/kg body weight.
[b] Intravenous doses administered daily for 14 days by tail vein injection at 22 mg/kg body weight.
[c] Significantly different from saline control group (P < 0.05) ; Student's test.

TABLE 3

Activity of aromatic amidines against *Pneumocystis carinii* pneumonia.

$$\text{HN=C(NH}_2\text{)-C}_6\text{H}_3\text{(R)-O-(CH}_2\text{)}_n\text{-O-C}_6\text{H}_3\text{(R)-C(NH}_2\text{)=NH}$$

| Compound | n | R | ORAL DOSING[a] cysts/g lung ± S.E. × 10$^6$ | % saline | # rats | IV DOSING[b] mean histological score[c] rats | # |
|---|---|---|---|---|---|---|---|
| Saline | — | — | 37.78 + 9.49 | 100.00 | 6 | 3.2 | 72 |
| Pentamidine | 5 | H | 64.36 + 25.35 | 170.35 | 6 | 1.1 | 63 |
| 9 | 3 | H | 16.43 + 6.36 | 43.49 | 6 | 0.9 | 8 |
| 10 | 3 | OCH$_3$ | 3.20 + 0.58 | 8.47 | 6 | 0.6 | 8 |
| 11 | 4 | H | 17.39 + 7.03 | 46.03 | 6 | 0.5 | 8 |

[a] Oral doses administered daily for 14 days by gavage @33 μmol/kg body weight.
[b] Intravenous doses administered daily for 14 days by tail vein injection @ 10 mg/kg body weight. Compound 10 given at 5 mg/kg.
[c] Data reprinted from J. Med. Chem. 33:1252 (1990). The histological score was determined subjectively from cysts detected in stained lung sections. Scores range from a low infection score of 0.5 to a high of 4.0.

EXAMPLE 6

Reduced Acute Toxicity of Amidoximes

The amidoximes tested have greatly reduced acute toxicity compared to the corresponding amidines. Acute toxicity was assessed in a dose escalation study using non-corticosteroid suppressed rats. Rats treated with one intravenous or oral dose of the test compound were monitored closely for 30 minutes for signs of overt toxic responses (see R. R. Tidwell et al., *J. Protozool.* 36.74S–76S (1989); R. R. Tidwell et al., *J. Med. Chem.* 33,1252 (1990)), then checked at one and 24 hours post-treatment. Single intravenous injections of the amidine compounds 8–10 produced overt symptoms (including muscle spasms, tremors, ataxia, dyspnea, hypoactivity) in test animals beginning at 40 μmol/kg. In contrast, intravenous injections of the corresponding amidoximes (Compounds 4a–4c) at four-fold higher dosages produced only minor symptoms. In addition, no overt acute toxic responses were observed for any rat treated orally by garage with the amidoximes (Compounds 4a–4c), with a maximum tested dose of 160 μmol/kg.

The foregoing is illustrative of the present invention and is not to be construed to be limiting thereof. The invention is defined by the following claims, with equivalents of the claims to be included herein.

That which is claimed is:

1. A method of treating *Pneumocystis carinii* pneumonia in a subject in need of such treatment, comprising orally administering to said subject a bis-benzamidoxime of Formula I:

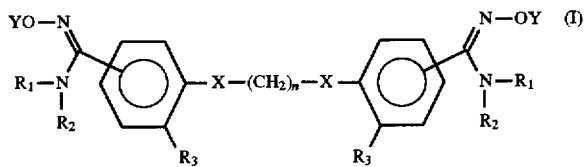

wherein:

$R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl;

$R_3$ is H, loweralkyl, oxyalkyl, alkoxyalkyl, hydroxyalkyl, cycloalkyl, aryl, aminoalkyl, alkylaminoalkyl or halogen;

n is from 2 to 6;

X is O, N, or S; and

Y is H or loweralkyl;

or a pharmaceutically acceptable salt thereof, wherein said benzamidoxime is reduced in said subject to produce a benzamidine having anti-*P. carinii* activity, and wherein said compound of Formula I is administered in an amount effective to treat *Pneumocystis carinii* pneumonia, with the proviso that said bis-benzamidoxime is not 1,5-bis-(4'-(N-hydroxy amidino)phenoxy)pentane.

2. The method according to claim 1, wherein said subject is afflicted with *Pneumocys carinii* pneumonia.

3. The method according to claim 1, wherein said subject is at risk of developing *Pneumocystis carinii* pneumonia and said compound is administered in a prophylactically effective amount.

* * * * *